United States Patent [19]

Quinn et al.

[11] Patent Number: 5,125,897
[45] Date of Patent: Jun. 30, 1992

[54] GASTROSTOMY DEVICE WITH ONE-WAY VALVE AND CUFF PIN

[75] Inventors: David G. Quinn, Grayslake; Erik Andersen, Vernon Hills; Steven E. Wendland, Rolling Meadows, all of Ill.

[73] Assignee: Corpak, Inc., Wheeling, Ill.

[21] Appl. No.: 515,855

[22] Filed: Apr. 27, 1990

[51] Int. Cl.[5] .................................. A61M 29/00
[52] U.S. Cl. ..................... 604/99; 604/175; 604/247; 604/256
[58] Field of Search ............... 600/31, 32; 604/51, 54, 93, 96, 99, 174, 175, 178, 247, 256, 264; 606/194

[56] References Cited

U.S. PATENT DOCUMENTS

| 3,583,404 | 6/1971 | McWhorter | 604/247 X |
| 3,726,283 | 4/1973 | Dye et al. | 604/247 X |
| 3,742,960 | 7/1973 | Dye et al. | 604/247 X |
| 4,344,434 | 8/1982 | Robertson | 604/175 X |
| 4,393,873 | 7/1983 | Nawash et al. | 604/174 X |
| 4,553,959 | 11/1985 | Hickey et al. | 604/96 |
| 4,668,225 | 5/1987 | Russo et al. | 604/270 |
| 4,685,901 | 8/1987 | Parks | 604/96 |
| 4,850,953 | 7/1989 | Haber et al. | 600/32 |
| 4,863,438 | 9/1989 | Gauderer et al. | 604/247 |
| 4,900,306 | 2/1990 | Quinn et al. | 604/97 |
| 4,944,732 | 7/1990 | Russo | 604/247 |
| 5,009,639 | 4/1991 | Keymling | 604/96 |

FOREIGN PATENT DOCUMENTS 8800816 2/1988 World Int. Prop. O. ............ 600/32

Primary Examiner—John D. Yasko
Assistant Examiner—Adam J. Cermak
Attorney, Agent, or Firm—Wallenstein, Wagner & Hattis, Ltd.

[57] ABSTRACT

A unique device for long term percutaneous enteral feeding through a surgically formed stoma, such as a gastrostomy, includes a tubular member having a fluid lumen and an inflation lumen. One end of the tubular member is perpendicularly joined to a retention platform through which passes an ambient air port for the inflation lumen and an inlet for the fluid lumen. Another end of the tubular member is provided with an outlet for the fluid lumen. A one-way valve on the outlet prevents reflux of gastric contents into the fluid lumen. Disposed near the one end of the tubular member is an inflatable member, inflatable and deflatable through the inflation lumen. The inflatable member provides retention and anchoring of the device within the patient's stomach.

5 Claims, 2 Drawing Sheets

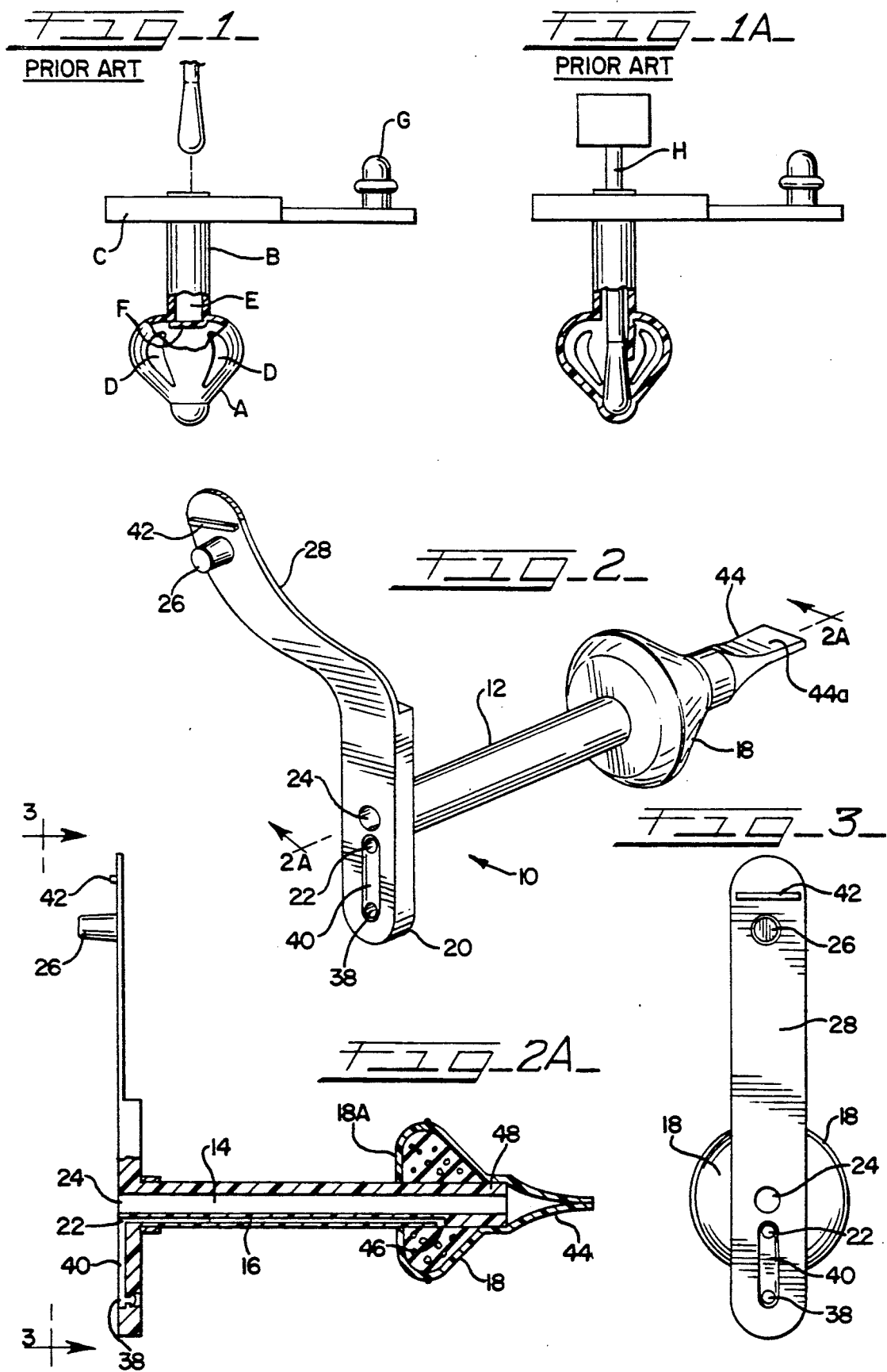

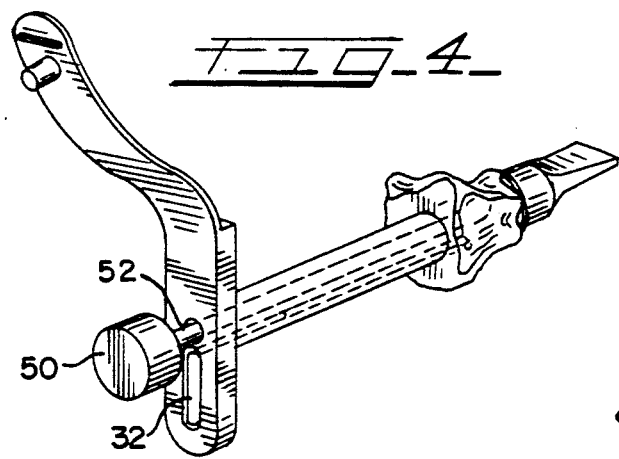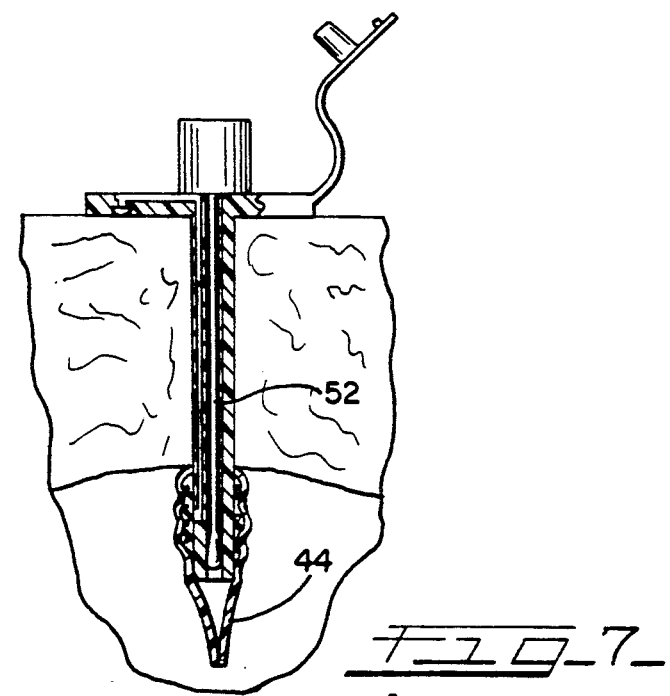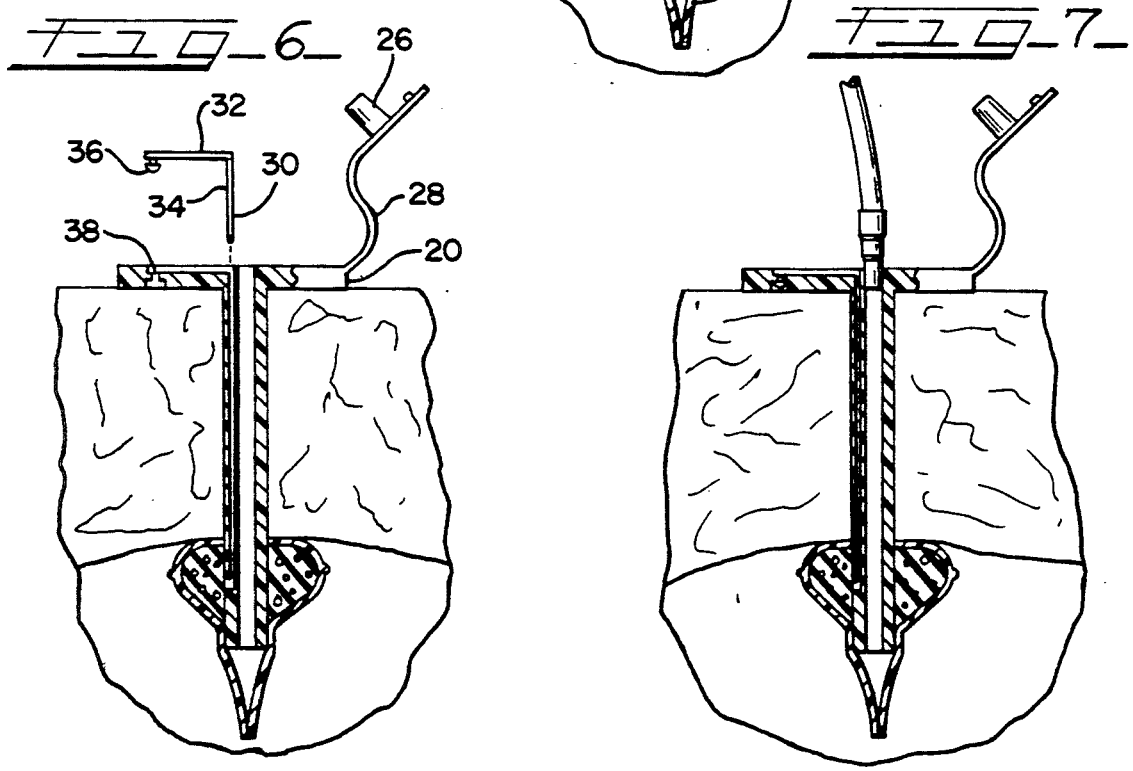

GASTROSTOMY DEVICE WITH ONE-WAY VALVE AND CUFF PIN

TECHNICAL FIELD OF THE INVENTION

The present invention generally relates to devices used for percutaneous enteral feeding and, in particular, to a device facilitating percutaneous enteral feeding through a gastrostomy.

BACKGROUND OF THE INVENTION

For patients having chronic or acute nutritional needs, percutaneous enteral feeding through a surgically formed ostomy, such as a gastrostomy is often indicated. The gastrostomy is typically formed through use of a percutaneous endoscopic technique and intubated with a gastrostomy tube to effect enteral feeding. U.S. Pat. Nos. 4,795,430 and 4,900,306 are examples of percutaneous endoscopic gastrostomy tubes using an inflatable cuff as a means of anchoring the tube within the gastrostomy.

After initial formation and intubation of the gastrostomy, it is often necessary to replace the gastrostomy tube with a device more suitable to long term feeding needs. These devices characteristically have a low structural profile to be carried closely to the abdominal wall of the patient without discomfort or snagging of clothing. When not in use for enteral feeding, a closure is provided to seal the feeding tube.

An example of one such prior art gastrostomy device is seen in FIGS. 1 and 1A. The prior art device of FIGS. 1 and 1A utilizes a deformable retention pod A which joins an enteral feeding tube B to a retention disk C. Retention pod A is provided with feeding ports D for access into fluid lumen E. To prevent reflux of gastric contents into fluid lumen E, a one-way flapper valve F is provided within pod A. When not being used during enteral feeding, plug G which is carried on retention disk C is inserted into the fluid lumen E.

FIGS. 1 and 1A also disclose a method of intubating a prior art gastrostomy device. An obturator or stylet H is inserted through the fluid lumen and seats within pod A. As the pod passes through the stoma of the gastrostomy, the pod is deformed by the inner walls of the stoma until passing into the stomach at which point the pod assumes an operative configuration. There are many problems associated with the prior art gastrostomy device as disclosed in FIGS. 1 and 1A and other similar devices.

One such problem is that during intubation, the obturator or stylet damages the anti-reflux flapper valve by deforming the valve hinge. As a result, the valve does not fully return to a tightly closed position permitting reflux of gastric contents into the fluid lumen with possible leakage outside of the patient. In addition, a flapper valve limits full utilization of the fluid lumen, thereby restricting fluid flow and impeding accurate fluid infusion. Likewise, the prior art gastrostomy device of FIGS. 1 and 1A also limits fluid effusion by the use of feeding ports D in pod A. These ports inherently restrict effusion of nutritional fluid from the fluid lumen by requiring some fluid to initially backfill the pod before fluid can effuse through the ports. Finally, intubation is made more difficult as the outer configuration and outer dimensions of deformable pod A do not reduce sufficiently to facilitate an easy and a traumatic intubation.

Hence, prior to the development of the present invention, a need existed for a gastrostomy feeding device which addresses these and problems associated with prior art devices.

SUMMARY OF THE INVENTION

According to the present invention, an improved gastrostomy device for long term percutaneous enteral feeding has been developed which solves the problems of prior art devices. Generally, the gastrostomy device of the present invention utilizes an inflatable retention member, such as a foam-filled cuff, for anchoring and retaining the distal end of the gastrostomy device within the stomach of a patient. The inflatable retention member, can be deflated to assume an essentially edge-free outer configuration which facilitates passage of the gastrostomy device through the stoma. When inflated, the retention member assumes an outer configuration having at least one flat surface for abutment against the inner wall of the patient's stomach.

The feeding tube joined to the retention member includes an inflation lumen which is disposed at one end to the retention member and a feeding lumen for infusion of enteral nutritional solutions to the patient. At one end the feeding tube has a port to dispose the inflation lumen to ambient air. At an other end, the feeding tube has an outlet to convey fluid from the fluid lumen into the patient. Means are provided for sealing the ambient air port of the tube to facilitate inflation of the retention member and to maintain the retention member in a deflated state. Preferably, the means for sealing the ambient air port includes a pin having a stem which occludes the inflation lumen. Perpendicularly joined to one end of the stem is a gripping member.

The one end of the feeding tube is provided with a retention platform such that upon intubation, the retention platform rests on the abdominal wall of the patient. An inlet for the fluid lumen is disposed through the retention platform and a plug for sealing the fluid lumen is carried on the retention platform. Also, disposed through the retention platform is the ambient air port of the inflation lumen which is laterally off-set from the feeding lumen inlet.

Unlike prior art gastrostomy devices, the present invention utilizes a one-way anti-reflux valve which is externally carried on the outlet end of the feeding tube distal from the inflatable member. The one-way valve, preferably a duck bill valve, is secured to the outer diameter of the tube outlet. During intubation of the gastrostomy device of the present invention, the stylet does not reach the valve to cause any valve damage. Rather during intubation, the valve is deflected to one side which maintains the valve in a closed state and prevents valve damage.

Finally, means are provided for securing the gripping member of the pin to the retention platform. Preferably such means includes a flanged fastening head carried on one end of the gripping member which seats within the grooved opening on the retention platform. The ambient air port for the inflation lumen and the opening are laterally aligned on the retention platform and preferably lie within a groove countersunk into the surface of the retention platform. As a result, when the pin member is fully inserted into the inflation lumen, the gripping member of the pin lies within the countersunk groove so that the gripping member becomes flush with the surface of the retention platform.

Other advantages and aspects of the invention will become apparent upon making reference to the specification, claims, and drawings to follow.

BRIEF DESCRIPTION OF THE DESCRIPTIONS

FIG. 1 is a side elevational view disclosing in partial vertical section a prior art gastrostomy device;

FIG. 1A is the same view of FIG. 1 disclosing a further vertical section of a prior art gastrostomy device;

FIG. 2 is a perspective view of one embodiment of a gastrostomy device of the present invention;

FIG. 2A is a vertical section view taken along line 2A—2A of FIG. 2;

FIG. 3 is a side elevational view taken along line 3—3 of FIG. 2A;

FIG. 4 is the same view as FIG. 2 disclosing a deflated retention member as used in the present invention;

FIG. 5 is a partial vertical sectional view disclosing intubation of one embodiment of the present invention;

FIG. 6 discloses re-inflation of the retention member shown in FIG. 5; and,

FIG. 7 discloses use of one embodiment of the present invention for percutaneous enteral feeding.

DETAILED DESCRIPTION OF THE INVENTION

While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspect of the invention to embodiment illustrated.

Referring now to the drawings, FIG. 2 discloses a preferred embodiment of a gastrostomy device 10 of the present invention. An enteral feeding tube 12 having, as disclosed in FIG. 2A, a fluid lumen 14 and an inflation lumen 16 joins an inflatable retention member 18 with a semi-flexible retention platform 20. To accommodate the inner dimensions of most surgically formed ostomies, feeding tube 12 preferably should have about an 12-30 French diameter.

As disclosed in FIGS. 2, 2A and 3, inflation lumen 16 is provided with a port 22 which passes through retention platform 20. Port 22 places lumen 16 in communication with ambient air and permits inflation of member 18 in a manner to be later described in greater detail. Likewise, fluid lumen 14 is provided with an inlet 24 which passes through retention platform 20. Inlet 24 is provided with inner dimensions to receive a male luer tip of an enteral feeding tube in the manner disclosed in FIG. 7. When a patient is not undergoing enteral feeding, a plug 26 carried on a strap 28 carried on retention platform 20 provides a secure closure of inlet 24.

When inflation lumen 16 is not being utilized to inflate or maintain the deflation of member 18, a pin 30 passes through ambient air port 22 to occlude inflation lumen 16. As best disclosed in FIG. 6, pin 30 includes a gripping member 32 perpendicularly joined to a stem 34 of pin 30. One end of gripping member 32 is provided with a flanged fastening head 36 which seats within a grooved opening 38 carried on retention platform 20. For ease of manufacturing, opening 38 may pass entirely through retention platform 20.

Pin 30 can be maintained securely within inflation lumen 16 without risk of dislodgement, accidental removal or without gripping member 32 becoming snagged on a patient's garments or bed sheets. In particular, ambient air port 22 and opening 38 are each countersunk and lie within a countersunk groove 40 as disclosed in FIGS. 2, 2A and 3. Countersunk groove 40 lies below the top surface of retention platform 20. When pin 30 is fully seated within inflation lumen 16, gripping member 32 lies within countersunk groove 40 to position gripping member 32 below the top surface of retention platform 20. Fastening head 36 securely seats within opening 38 to assure that gripping member 32 lies within countersunk groove 40. Strap 28 also carries a raised rib 42 such that when plug 26 is seated within enteral feeding inlet 24, ridge 42 presses against gripping member 32 to maintain its positioning within countersunk groove 40. To release fastening head 36 from opening 38, the user downwardly bends an edge of retention platform 20, nearest to opening 38, which forces head 36 out of opening 38. This exposes a free end of gripping member 32 allowing a user to grasp gripping member 32 and withdraw pin 30 out of the inflation lumen.

All embodiments of the present invention include a one-way, anti-reflux valve 44 carried on outlet 48 of enteral feeding tube 12 distal to inflation member 18. Preferably, valve 44 is a duck bill valve which prevents reflux of gastric contents into feeding lumen 14. Unlike the prior art gastrostomy devices which utilize a flapper valve or other asymmetric valve internally positioned within the gastrostomy device, the present invention utilizes a symmetric one-way valve externally carried on the outlet of the feeding tube. As best disclosed in FIGS. 2A, 6 and 7, valve 44 is secured to the outer diameter of tube 12 near outlet 48. By so doing, fluid flow through fluid lumen 14 is unrestricted and a high rate of fluid effusion is maintained. As will also be explained later in greater detail, valve 44 does not incur any damage during intubation of device 10 through use of an obturator or stylet is used. Preferably, valve 44 is one piece and made from a vacuum forming method which assures that valve 44 is tightly resealable, yet each leaf 44a responds to fluid flow. Preferably valve 44 is bonded to outlet end 48 of feeding tube 12.

Inflatable retention member 18 is substantially foam-filled and is placed in communication with inflation lumen 16 through a duct 46 as disclosed in FIG. 2A. As disclosed in FIG. 4, when in a deflated state, inflatable retention member 18 has an essentially edge-free outer configuration which facilitates passage of retention member 18 through the stoma of the gastrostomy. Upon inflation of retention member 18, a generally flat surface 18a is created which abuts against the stomach wall of the patient as disclosed in FIGS. 5 through 7.

FIGS. 4 through 7 disclose a method of using a preferred embodiment of gastrostomy device 10 of the present invention. First, pin 30 is removed from inflation lumen 16 and a user deflates retention member 18 by its compression. Retention member 18 is maintained in a compressed state by re-insertion of pin 30 into inflation lumen 16. Next, an obturator or stylet 52 such as that shown in FIG. 4 having a gripping head 50 is inserted into inlet 24 of fluid lumen 14. As shown in FIG. 5, the tip of obturator 52 stops short of passing into valve 44. Obturator head 50 abuts against the top surface of retention platform 20 and with retention member in a deflated state, the user inserts gastrostomy device 10 through the stoma until retention platform 20 rests on the external abdominal wall of the patient as disclosed in FIGS. 5 through 7. The thickness of cutaneous and subcutaneous tissue can vary for adult, pediatric and geriatric patients. Hence, it is necessary prior to intubation of gastrostomy device 10 to determine the depth of the ostomy prior to intrubation. A length of enteral feeding tube 12 appropriate to the thickness of cutaneous and subcutaneous tissue of the patient should be selected. During intubation through the patient's stoma, valve 44, preferably being a duck bill valve, flexes to one side to facilitate intubation without any damage to the sealability or operation of valve 44.

Upon intubation of gastrostomy device 10, obturator 48 is withdrawn from feeding lumen 14. As disclosed in FIG. 6, pin 30 is removed from inflation lumen 16 to permit ambient air pressure to passively re-inflate retention member 18. Upon re-inflation of retention member 18, pin 30 is re-inserted into inflation lumen 16 in the manner disclosed in FIG. 7. By doing so the inflation lumen is sealed and maintains retention member 18 in an inflated state to anchor gastrostomy device 10 against the patient's stomach wall. As shown in FIG. 7, an enteral feeding tube having a Luer connector may then be inserted into inlet 24 of fluid lumen 14 or when not feeding, plug 26 on strap 28 is inserted into inlet 24.

While the invention has been described with reference to a preferred embodiment, it will be understood by those skilled in the art that various changes may be made and equivalents may be substituted for elements thereof without departing from the broader aspects of the invention. Also, it is intended that broad claims not specifying details of particular embodiment disclosed herein as the best mode contemplated for carrying out the invention should not be limited to such details.

We claim:

1. A device for percutaneous enteral feeding through a surgically formed ostomy, comprising:

a tube having at least a fluid lumen and an inflation lumen, the tube having aport near one end to dispose the inflation lumen to ambient air and an outlet at an other end to convey fluid from within the fluid lumen into a patient;

an inflatable member joined near the other end of the tube, the member being inflatable and deflatable through the inflation lumen, the member in a deflated state having an outer configuration facilitating passage through the stoma, the member in an inflated state facilitating retention of the device within the ostomy;

one-way valve means secured to the outlet of the tube, the valve means being responsive to fluid flowing through the fluid lumen;

means for sealing the ambient air port, the means including;

a pin member having a stem, the stem being dimensioned to occlude the ambient air port and inflation lumen; and, a gripping member perpendicularly joined to one end of the stem; and, means for sealing the fluid lumen at the one end of the tube.

2. The device of claim 1 further including a retention platform perpendicularly joined to the one end of the tube, and means for securing the gripping member to the retention platform.

3. The device of claim 2 wherein the gripping member includes a fastening head which removably seats within an opening on the retention platform.

4. The device of claim 3 wherein the opening is laterally aligned with the ambient air port by a distance equal to the length of the gripping member.

5. The device of claim 4 wherein the ambient air port and the opening lie within a groove countersunk into the surface of the retention platform.

* * * * *